(12) United States Patent
Png et al.

(10) Patent No.: US 10,555,841 B2
(45) Date of Patent: Feb. 11, 2020

(54) FABRIC, PROTECTIVE GARMENTS MADE THEREFROM, AND METHODS OF MAKING

(71) Applicant: Moonrise Sisters, Inc., New York, NY (US)

(72) Inventors: Enqin Eunice Png, Providence, RI (US); Julie M. Sygiel, New York, NY (US); Daniel M. Wyner, North Scituate, RI (US)

(73) Assignee: Moonrise Sisters, Inc., New York, NY (US)

( * ) Notice: Subject to any disclaimer, the term of this patent is extended or adjusted under 35 U.S.C. 154(b) by 778 days.

(21) Appl. No.: 15/015,865

(22) Filed: Feb. 4, 2016

(65) Prior Publication Data

US 2016/0296384 A1 Oct. 13, 2016

Related U.S. Application Data

(63) Continuation of application No. 12/749,504, filed on Mar. 29, 2010, now abandoned.

(60) Provisional application No. 61/164,000, filed on Mar. 27, 2009.

(51) Int. Cl.
*A61F 13/49* (2006.01)
*A61F 13/511* (2006.01)
*A61F 13/513* (2006.01)
*A61F 13/51* (2006.01)

(52) U.S. Cl.
CPC ............ *A61F 13/49* (2013.01); *A61F 13/511* (2013.01); *A61F 13/513* (2013.01); *A61F 13/52* (2013.01); *A61F 2013/51061* (2013.01); *A61F 2013/51139* (2013.01); *A61F 2013/51322* (2013.01)

(58) Field of Classification Search
CPC .............. A61F 13/49006; A61F 13/496; A61F 13/49003; A41B 2400/60; A41B 2400/62; A41B 2400/20; A41B 2400/22; A41B 2500/54
USPC ............................. 604/358–402; 2/400, 406
See application file for complete search history.

(56) References Cited

U.S. PATENT DOCUMENTS

| 3,123,075 | A | | 3/1964 | Stamberger |
| 3,599,640 | A | | 8/1971 | Larson |
| 3,909,851 | A | * | 10/1975 | Garrou .................. A41B 11/14 2/409 |

(Continued)

FOREIGN PATENT DOCUMENTS

| EP | 0 619 953 A1 | 10/1994 |
| GB | 2 176 692 | 1/1987 |

(Continued)

OTHER PUBLICATIONS

Technology Shearing, www.danti.it/010981.asp, accessed Jul. 28, 2015 (Year: 2008).*

(Continued)

*Primary Examiner* — Peter S Vasat
(74) *Attorney, Agent, or Firm* — Wolf, Greenfield & Sacks, P.C.

(57) ABSTRACT

Disclosed herein are protective garments comprising an inner surface or portion of an inner surface with both absorbent and stain resistant properties while maintaining the soft feel, breathability and aesthetic properties associated with traditional "non protective" intimate apparel. The fabrics and methods of constructing the garments are also disclosed herein.

25 Claims, 10 Drawing Sheets

(56) References Cited

U.S. PATENT DOCUMENTS

| | | | |
|---|---|---|---|
| 4,324,246 A * | 4/1982 | Mullane | A61F 13/512 604/366 |
| 4,636,207 A | 1/1987 | Buell | |
| 4,809,493 A | 3/1989 | Genba et al. | |
| 4,880,424 A | 11/1989 | Rautenber | |
| 4,897,084 A | 1/1990 | Ternstrom et al. | |
| 4,923,454 A * | 5/1990 | Seymour | A61F 13/15642 604/368 |
| 5,098,419 A | 3/1992 | Gold | |
| 5,176,672 A | 1/1993 | Bruemmer et al. | |
| 5,185,011 A | 2/1993 | Strasser | |
| 5,244,716 A | 9/1993 | Thornton et al. | |
| 5,268,004 A * | 12/1993 | Greak | A41D 31/00 8/115.56 |
| 5,290,269 A * | 3/1994 | Heiman | A61F 5/485 604/372 |
| 5,344,698 A | 9/1994 | Rock et al. | |
| 5,360,422 A | 11/1994 | Brownlee et al. | |
| 5,392,467 A | 2/1995 | Moretz et al. | |
| 5,414,870 A | 5/1995 | Moretz et al. | |
| 5,416,929 A | 5/1995 | Braunstein | |
| 5,466,515 A | 11/1995 | Blauer et al. | |
| 5,514,459 A | 5/1996 | Blauer et al. | |
| 5,546,607 A | 8/1996 | Roberts | |
| 5,562,648 A | 10/1996 | Peterson | |
| 5,593,754 A | 1/1997 | Blauer et al. | |
| 5,609,588 A | 3/1997 | DiPalma et al. | |
| 5,626,949 A | 5/1997 | Blauer et al. | |
| 5,830,202 A | 11/1998 | Bogdanski et al. | |
| 5,944,708 A | 8/1999 | Philpott | |
| 6,041,446 A | 3/2000 | Braunstein et al. | |
| 6,195,800 B1 | 3/2001 | Gilmer et al. | |
| 6,336,221 B1 | 1/2002 | Blauer et al. | |
| 6,490,734 B2 | 12/2002 | Blauer et al. | |
| 6,610,901 B2 * | 8/2003 | McMahon-Ayerst | A41B 9/12 604/378 |
| 6,676,648 B2 | 1/2004 | Bruemmer Prestley et al. | |
| 6,745,405 B2 | 6/2004 | Blauer et al. | |
| 6,782,557 B1 * | 8/2004 | Feder | A61F 13/15268 2/400 |
| 6,786,798 B1 | 9/2004 | Gendel | |
| 6,848,121 B1 | 2/2005 | Halid | |
| 7,361,803 B2 | 4/2008 | Miskie | |
| 2002/0122890 A1 * | 9/2002 | Linford | D06M 7/00 427/389.9 |
| 2003/0125689 A1 | 7/2003 | Olson et al. | |
| 2004/0185748 A1 | 9/2004 | Gendel | |
| 2006/0070163 A1 | 4/2006 | Beck et al. | |
| 2007/0142803 A1 * | 6/2007 | Soerens | A61F 13/531 604/368 |
| 2007/0142816 A1 | 6/2007 | Carstens | |
| 2008/0114327 A1 | 5/2008 | Barge | |
| 2008/0222781 A1 | 9/2008 | Rhew | |
| 2008/0276352 A1 | 11/2008 | Strange et al. | |
| 2008/0282450 A1 | 11/2008 | Suga et al. | |
| 2010/0198178 A1 | 8/2010 | Litvay | |
| 2010/0249736 A1 | 9/2010 | Png et al. | |
| 2014/0025027 A1 | 1/2014 | Png et al. | |

FOREIGN PATENT DOCUMENTS

| | | | |
|---|---|---|---|
| GB | 2176692 A * | 1/1987 | A41B 9/00 |
| GB | 2 311 714 | 8/1997 | |
| WO | WO 86/02543 | 5/1986 | |
| WO | WO 00/02511 A1 | 1/2000 | |

OTHER PUBLICATIONS

"Definition of Mild, Moderate and Severe Incontinence on the 24-hour pad test", BJOG: an International Journal of Obstetrics and Gynaecology Aug. 2004, vol. 111, pp. 859-862. (Year: 2004).*
Cotton, facts and general information from Swicofil, http://www.swicofil.com/products/001cotton.html (Year: 2015).*
"Quantifying Wetting and Wicking Phenomena in Cotton Terry as Affected by Fabric Conditioner Treatment." Textile Research Journal 72.5 (2002): 423-28. (Year: 2002).*
International Search Report and Written Opinion for International Application No. PCT/US2010/029110, dated May 20, 2010.
Written Opinion for International Application No. PCT/US2011/053459, dated Jan. 18, 2012.
Extended European Search Report for Application No. EP 10 75 7004, dated Apr. 23, 2014.
[No Author Listed] Protec-Style Designs Marilyn Monroe-Inspired Panty. Global Intimate Wear. http://news.globalintimatewear.com/Sales/2413/Protec_Style_Designs_Marilyn_Monroe_Inspired_Panty.html [accessed Jul. 17, 2013]. 3 pages.
[No Author Listed] BFF "Period Undies" An Essential Part of Every Woman's Wardrobe!. Necessit-ease. http://www.necessit-ease.com/index.html [accessed via the WayBack Machine on Jul. 15, 2013].
[No Author Listed] Finally, Some Oops-Free Underwear. SHEfinds. http://www.shefinds.com/2008/finally_some_oops_free_underwear_thank_you_ongossamer_luxury_liner/# [accessed Jul. 12, 2013]. 2 pages.
[No Author Listed] Technology Shearing. www.danti.it/010981.asp [accessed Jul. 28, 2015]. 2 pages.
O'Sullivan et al., Definition of Mild, Moderate and Severe Incontinence on the 24-hour pad test. BJOG: An International Journal of Obstetrics and Gynaecology. Aug. 2004; 111:859-62.
[No Author Listed] Cotton—Facts and general information from Swicofil. Swicofil. http://www.swicofil.com/products/001cotton.html [Accessed Jul. 28, 2015]. 7 pages.
Van Der Meeren et al., Quantifying Wetting and Wicking Phenomena in Cotton Terry as Affected by Fabric Conditioner Treatment. Textile Research Journal. May 2002:423-28.
[No Author Listed] Jumbo Elite Foldable Utility Cart. Comfort House. http://www.comforthouse.com/watlaunbag.html [accessed Jul. 30, 2010]. 2 pages.
[No Author Listed] Waterproof Underwear. Bruce Medical Supply. http://www.brucemedical.com/watunl.html [accessed Jul. 30, 2010]. 1 page.
[No Author Listed] Hi-Cut Stay-Dry Briefs. Bruce Medical Supply. http://www.brucemedical.com/hicstaybrief.html [accessed Jul. 6, 2012], 1 page.
[No Author Listed] Dynamic-Living.com. http://dynamic-living.com/waterproof-panties.html [accessed Jul. 30, 2010]. 2 pages.
[No Author Listed] Welcome to Fabrite International LLC. www.fabrite.com. [accessed printed Jul. 30, 2010]. 2 pages.
International Search Report and Written Opinion for Application No. PCT/US2011/053459 dated Jan. 18, 2012.
International Preliminary Report on Patentability for Application No. PCT/US2011/053459 dated Apr. 11, 2013.
International Preliminary Report on Patentability for Application No. PCT/US2010/029110 dated Oct. 6, 2011.
U.S. Appl. No. 13/876,105, filed Oct. 9, 2013, Png et al.

* cited by examiner

TABLE A -- FABRIC CHARACTERISTICS

| Fabric Function | Fabric Layer | Fabric Manufacturer and Style | Manufacturer's Reported Fabric Composition | Yarn Treatment | Fabric Treatment | Manufacturer's Reported Fabric Weight Range (oz/yd$^2$) | Measured Total Water Absorbency (g/m$^2$) (based on "Eulie Dip Test") | Measured Absorbent Capacity (ml) (based on "Eulie Capacity Test") |
|---|---|---|---|---|---|---|---|---|
| Absorbent | A | Darlington Fabrics Style 27210 | 76% 40/34 DL Nylon 24% 40 Denier Spandex | None | Lasting Degree WXSTV[1] | 3.7 - 4.1 | 347.2 | 31 |
| | B | Darlington Fabrics Style 27000 | 87% 70/34 Nylon 13% 40 Denier Spandex | None | Lasting Degree XXSTV[2] | 6.4 - 7.2 | 483.6 | 40 |
| | C | United Knitting Style 46322 | 86% Polyester 14% Lycra®[3] | Sorbtek®[4] | None | 7.0 | 806 | 37.5 |
| | 3 | Enviro Fabrics Style OCSJ 3040 | 92% Organic cotton 8% Spandex | None | 6.0% Amipel HGT (C) 8.0% Nepton EXT 84% water[5] | 6.9 - 7.2 | Not measured | Not measured |
| Repellent | 4 | Enviro Fabrics Style OCSJ 3040 LT | 92% Organic cotton 8% Spandex | None | same | 6.0 - 6.3 | Not measured | Not measured |
| | 5 | Darlington Fabrics Style 25590 | 80% 40/13 DL Nylon 20% Denier Spandex | None | XSTR | 5.2 - 5.8 | Not measured | Not measured |

FIG. 8

1 Available from Piedmont Chemical, North Carolina
2 Available from Piedmont Chemical, North Carolina
3 LYCRA is a registered trademark of Invista North America S.A.R.L., Corporation, Luxembourg
4 Sorbtek is a registered trademark of Unifi, Inc., North Carolina
5 Formulated by Applicants; Amipel HGT (C) and Nepton EXT are both available from Apollo Chemical Inc., North Carolina, a division of Mount Vernon Chemicals LLC QUALITATIVE PERFORMANCE COMPARED TO COMBINED FABRIC WEIGHT AND
PREDICTED TOTAL WATER ABSORBENCY

| Number of Layers | Fabric Layers 1/2/3/4/5* | Combined Fabric Weight (based on Manufacturer's Reported Weight) (oz/yd$^2$) | Predicted Total Water Absorbency of Combined Fabric Layers (g/m$^2$) | Comments on thickness Leakage results |
|---|---|---|---|---|
| 2 | A3 | 10.6 | 347.2 | N/A |
| | B3 | 13.3 | 483.6 | N/A |
| | C3 (Example 6) | 13.9 | 806 | Very thin; minimal leakage |
| 3 | AB3 (Example 2) | 17 | 830.8 | Thinness is appealing; 5/21 pairs leaked |
| | BA3 | 17 | 830.8 | Thin; 5/15 pairs leaked |
| | AC3 (Example 7) | 17.6 | 1153.2 | Felt thinner than AB3; minimal leakage (one leak, but improperly used) |
| | BB3 (Example 3) | 19.7 | 967.2 | Bordering on too thick; no leakage |
| 4 | AAA3 (Example 1) | 18 | 1041.6 | Feels thinner than combinations using Fabric B; no leakage |
| | AB44 (Example 4) | 19.1 | 830.8 | Too thick; no leakage |
| | BA44 | 19.1 | 830.8 | Too thick |
| | A4A4 | 19.4 | 694.4 | Bordering on too thick, 2/13 pairs leaked |
| | ABA3 (Example 5) | 20.7 | 1178 | No comments on thickness; 2/5 pairs leaked |
| | A3A3 | 21.2 | 694.4 | Bordering on too thick, 2/10 pairs leaked |
| | B4A4 | 22.1 | 830.8 | Too thick |
| | A4B4 | 22.1 | 830.8 | Too thick |
| | B4B4 | 24.8 | 967.2 | Too thick |
| 5 | AAAA3 | 21.7 | 1388.8 | Too thick; 1/6 leaked |
| | AA4A4 | 23.1 | 1041.6 | Too thick; 3/12 pairs leaked |
| | AAA44 | 23.1 | 1041.6 | Too thick |
| | AA3A3 | 24.9 | 1041.6 | Too thick |

* Layer 1 is the body-contacting layer

FIG. 9

| Working Example | Gusset Construction | | | Results | | | | |
|---|---|---|---|---|---|---|---|---|
| | Number of Layers | Layer Number | Fabric Type | Maximum Combined Projected Water Absorbency (g/yd²) (based on "Eulie Capacity Test") | Combined Fabric Weight (oz/yd²) | Absorbent Capacity of Combined Layers (ml) (based on "Eulie Capacity Test") | | Comments/Qualitative Results |
| | | | | | | Maximum Projected | Actual | |
| Example 1 | 4 | 1 | A | 1041.6 | 18 - 19.5 | 93 | 47 | 1) Adhesive from pads sticks to Fabric A - may need additional mesh layer 2) Fabric 3 provided added leakage protection in comparison to Fabric 4 (possibly due to slightly greater weight of Fabric 3) |
| | | 2 | A | | | | | |
| | | 3 | A | | | | | |
| | | 4 | 3 | | | | | |
| Example 2 | 3 | 1 | A | 830.8 | 17 - 18.5 | 71 | 40.3 | aesthetically pleasing thickness and soft top layer, but didn't prevent spills 100%; pad adhesive sticks to layer A |
| | | 2 | B | | | | | |
| | | 3 | 3 | | | | | |
| Example 3 | 3 | 1 | B | 967.2 | 19.7 - 21.6 | 80 | 47 | good performance, but aesthetics are outside desirable weight thickness and feel |
| | | 2 | B | | | | | |
| | | 3 | 3 | | | | | |
| Example 4 | 4 | 1 | A | 830.8 | 19.1 - 23.9 | 71 | 44.2 | no leaks but thickness is outside desirable range and top layer sticks to pad adhesive |
| | | 2 | B | | | | | |
| | | 3 | 4 | | | | | |
| | | 4 | 4 | | | | | |
| Example 5 | 4 | 1 | A | 1178 | 20.7 - 22.6 | 101 | 47 | similar aesthetic characteristics as A/B/3 but with added protection |
| | | 2 | B | | | | | |
| | | 3 | A | | | | | |
| | | 4 | 3 | | | | | |
| Example 6 | 2 | 1 | C | 806 | 13.9 - 14.2 | | 37.5 | thinnest reasonable candidate, top layer C isn't as soft as A but pad adhesive does not stick |
| | | 2 | 3 | | | | | |
| Example 7 | 3 | 1 | A | 1153.2 | 17.6 - 18.3 | | 49.5 | this combination almost same thinness as C/3 with a bit of added protection and a softer top layer |
| | | 2 | C | | | | | |
| | | 3 | 3 | | | | | |

\* In each Example, Layer 1 is the body-contacting gusset layer

FIG. 10

FABRIC, PROTECTIVE GARMENTS MADE THEREFROM, AND METHODS OF MAKING

RELATED CASES

This application is a continuation of and claims priority under 35 U.S.C. § 120 to U.S. patent application Ser. No. 12/749,504, filed Mar. 29, 2010 and entitled "FABRIC, PROTECTIVE GARMENTS MADE THEREFROM, AND METHODS OF MAKING," which claims priority under 35 U.S.C. § 119(e) to U.S. Provisional Patent Application No. 61/164,000, filed Mar. 27, 2009 and entitled "FABRIC, PROTECTIVE GRMENTS MADE THEREFROM, AND METHODS OF MAKING," which is incorporated herein by reference in its entirety.

TECHNICAL FIELD

The present disclosure is related to functional fabrics, protective garments made therefrom, particularly protective undergarments, and methods of making the foregoing.

BACKGROUND

Many varieties of feminine sanitary products have been commercialized, and are designed to absorb bodily discharges. For instance, sanitary napkins and tampons exist in many designs and iterations with slightly varying functions to absorb menstrual fluid. However, many products are not fully adequate, allowing menstrual discharges to leak onto women's inner and outer apparel, often leaving stubborn stains on the apparel, especially if allowed to dry before washing. Some women immediately may throw away stained undergarments, but many attempt to remove the stains using a variety of cleansers and techniques. Without thorough cleansing, stains may become permanent, which may be a source of embarrassment if others see the stains. When a leak extends to a woman's outerwear, it may require the involvement of a cleaning service, which is even more embarrassing.

Although leaks may occur at any time, women tend to experience them more often in the following two instances: on the first day of the menstrual cycle, when not yet wearing appropriate sanitary products, and when lying down, usually during sleep. However, various vaginal discharges with the potential to stain garments occur throughout the month.

Some undergarments have been designed to solve the issue of menstrual leaks and staining However, such products are either not adequately protective and have no barrier properties (offering only absorbent characteristics), or alternatively, they are constructed with barrier fabrics that are aesthetically unpleasing and uncomfortable.

Diapers and adult incontinence products are generally absorbent on the inside, but because they need to absorb very large amounts of liquid, they use thick pads where aesthetics are completely different from the constructions of the present concept. Because the fluid levels are highly varied and quite large in these products, they also use complete film barriers that are generally not air permeable. While these garments have some functionality, none of them are suitable for use as an undergarment for daily use.

There is a need for functional fabric and garments made therefrom that absorb fluid, prevent the transmission of fluid to outerwear, do not permanently stain, and additionally are sufficiently attractive and comfortable to wear on a daily basis in place of non-protective undergarments.

SUMMARY

The present disclosure is directed, in one embodiment, to a garment portion, comprising at least one absorbent layer comprising a body-contacting surface, and an absorbent capacity of at least about 300 g/m2; and at least one repellent layer disposed adjacent to the at least one absorbent layer and comprising an outer surface disposed opposite the body-contacting surface.

In another embodiment, the present disclosure is directed to a garment portion comprising at least one absorbent layer comprising a body-contacting surface; and at least one repellent layer disposed adjacent to the at least one absorbent layer and comprising an outer surface disposed opposite the body-contacting surface; wherein the garment portion comprises a combined weight of less than about 20 oz/yd2.

In another embodiment, the present disclosure is directed to a garment portion comprising at least one absorbent layer comprising a body-contacting surface; and at least one repellent layer disposed adjacent to the at least one absorbent layer and comprising an outer surface disposed opposite the body-contacting surface; wherein the garment portion comprises a combined absorbent capacity of at least about 40 ml.

Any one of the foregoing garment portions may be transmissive to air and/or transmissive to moisture vapor. One or both surfaces of the layers can comprise a napped, sueded or texturized surface, adapted to absorb fluid and to wick the absorbed fluid through to the adjacent layer.

The at least one absorbent layer and the at least one repellent layer can be a polymeric material or a microfiber material, and combinations thereof. The polymeric material can comprise polyolefins, polyamides, and combinations thereof.

The at least one repellent layer can comprise a water repellent finish, which may be a film having a thickness of less than about 10 microns (μm). In some embodiments, the film may be driven into the fabric by heat and pressure. The at least one repellent layer is a meltblown material such as a stretchable polymer such as polyurethane or co-polyether-ester, or a microfiber layer. The at least one repellent layer can comprise a fabric which has been coated or saturated with a silicone or polyurethane or other elastic water repellent polymer.

In some embodiments, the at least one absorbent layer and at least one repellent layer may be bonded together, and the bonding may be at an edge of each layer.

Another aspect of the disclosure is an undergarment comprising one of the foregoing garment portions, which is a gusset portion of the undergarment. The gusset can comprise a front edge, a side, a back edge and opposing side edges, and the front and back edges are attached to a front and a back of the undergarment at a front seam and a back seam. One or more of the front and back seams comprise an inverted triangular shape, and/or one or more of the front and back seams extend to an upper edge of the undergarment. In some embodiments, one or more of the front and back seams can comprise a hydrophobic coating. In other embodiments, one or more of the opposing edges can comprise a hydrophobic coating. In yet other embodiments, one or more of the front and back seams and one or more of the opposing edges can comprise a hydrophobic coating.

BRIEF DESCRIPTION OF THE DRAWINGS

Referring now to the figures, which are exemplary embodiments, and wherein like elements are numbered alike:

FIG. 8 is a table (Table A) listing the characteristics of various hydrophobic and hydrophilic fabrics;

FIG. 9 is a table (Table B) summarizing the qualitative results of panties constructed using various combinations of fabrics listed in FIG. 9; and FIG. 10 is a table (Table C) summarizing the absorbent capacity of selected panties from FIG. 10.

DETAILED DESCRIPTION

The present disclosure is directed to protective garments that provide leak resistance, fluid absorbance and fluid barrier characteristics. In some instances, the garments also may provide stain resistance and/or stain-releasing characteristics. The protective garments are stretchy and breathable, have a non-film like drape, and an attractive look and feel. Exemplary protective garments according to the present disclosure are protective undergarments, particularly women's protective undergarments, which can be made aesthetically attractive, similar to non-protective women's undergarments, thereby offering women the ability to wear the protective undergarments without discomfort or embarrassment.

The undergarments can comprise at least one layer of a fabric that is hydrophilic, or treated to be hydrophilic, disposed adjacent to at least one layer of fabric that is hydrophobic or treated to by hydrophobic. Alternatively, the undergarments can comprise a single layer of fabric with a first surface that is hydrophilic or treated to be hydrophilic, and second surface that is hydrophobic or treated to be hydrophobic, opposite the hydrophilic surface. The present garments are constructed to absorb and/or contain the volume of fluid from a woman's menstrual cycle, which may be in the range of 5-30 milliliters and varies, of course, depending on many factors.

The present garment construction does not require a film or coating, which tends to be uncomfortable or undesirable for the reasons noted above. The foregoing characteristics are accomplished with the use of unique functional fabrics and garment constructions. The present undergarments provide effective leak resistance against and/or act as a fluid barrier against blood spills, while remaining breathable and stretchable.

In certain embodiments, the fabrics may be stretchable knit fabrics, which provide leak resistance and/or act as a fluid barrier, in the absence of a film or coating. The use of such fabrics for leak resistance and/or as a fluid barrier is unique, with or without the use of elastane (e.g., Lycra) in the fabric.

Figure 1:
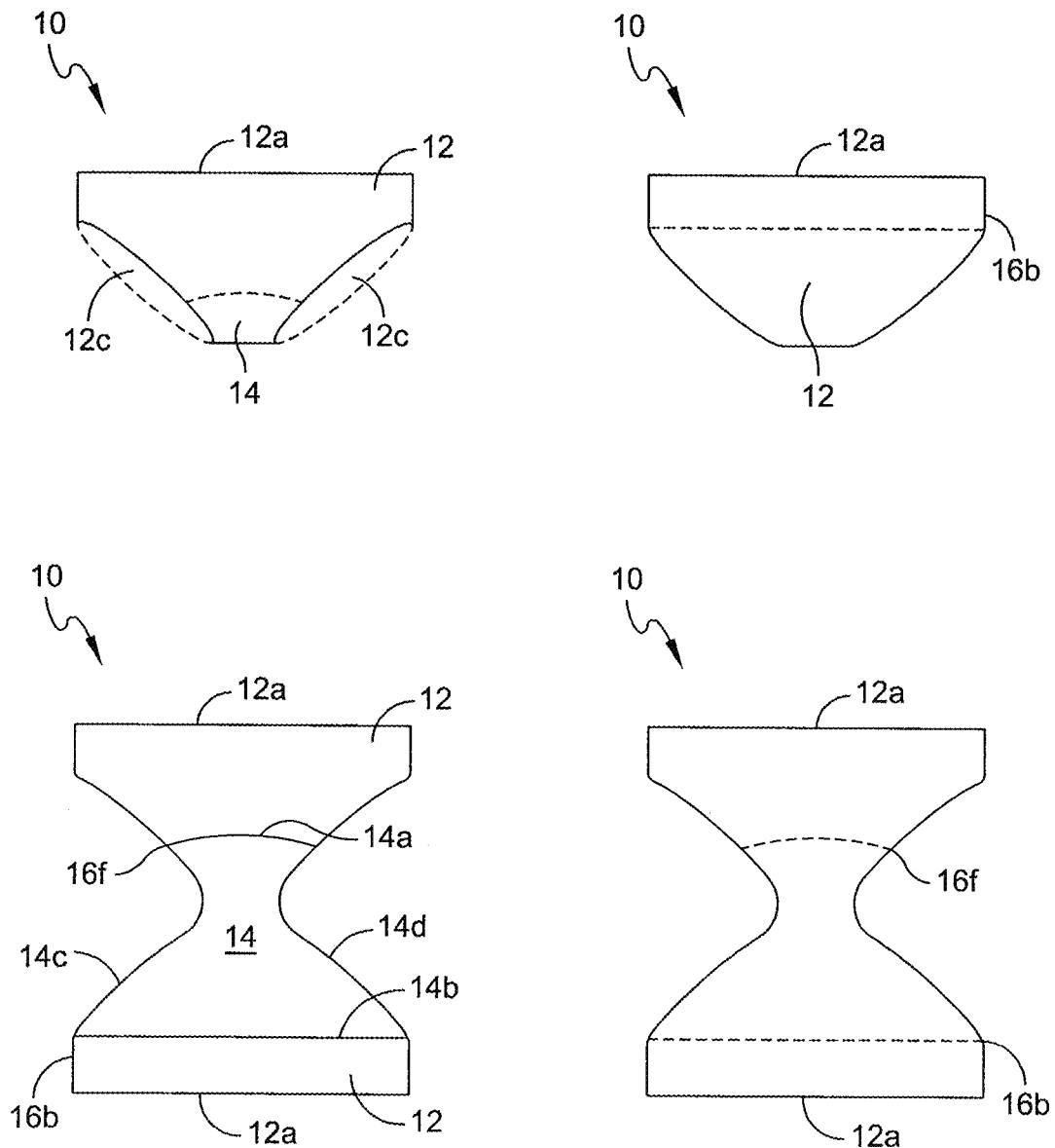
FIG. 1 shows front, back, interior and exterior views of one exemplary garment according to the present disclosure.

FIG. 1 shows an exemplary embodiment of an undergarment 10 according to the present disclosure, which will be referred to hereinafter for ease of illustration as a panty 10. Panty 10 comprises a body portion 12 and a gusset region 14. Body portion 12 comprises an upper edge 12a defining a waistband, and two leg openings 12c. Gusset region 14 comprises front and back edges 14a,b, and opposing side edges 14c,d. Gusset region 14 is attached to the body portion 12 at the front and back edges 14a,b, defining a front seam 16f and a back seam 16b. Gusset region 14 comprises a functional material 100 according to the present disclosure, as will be described in further detail below.

Figure 2:
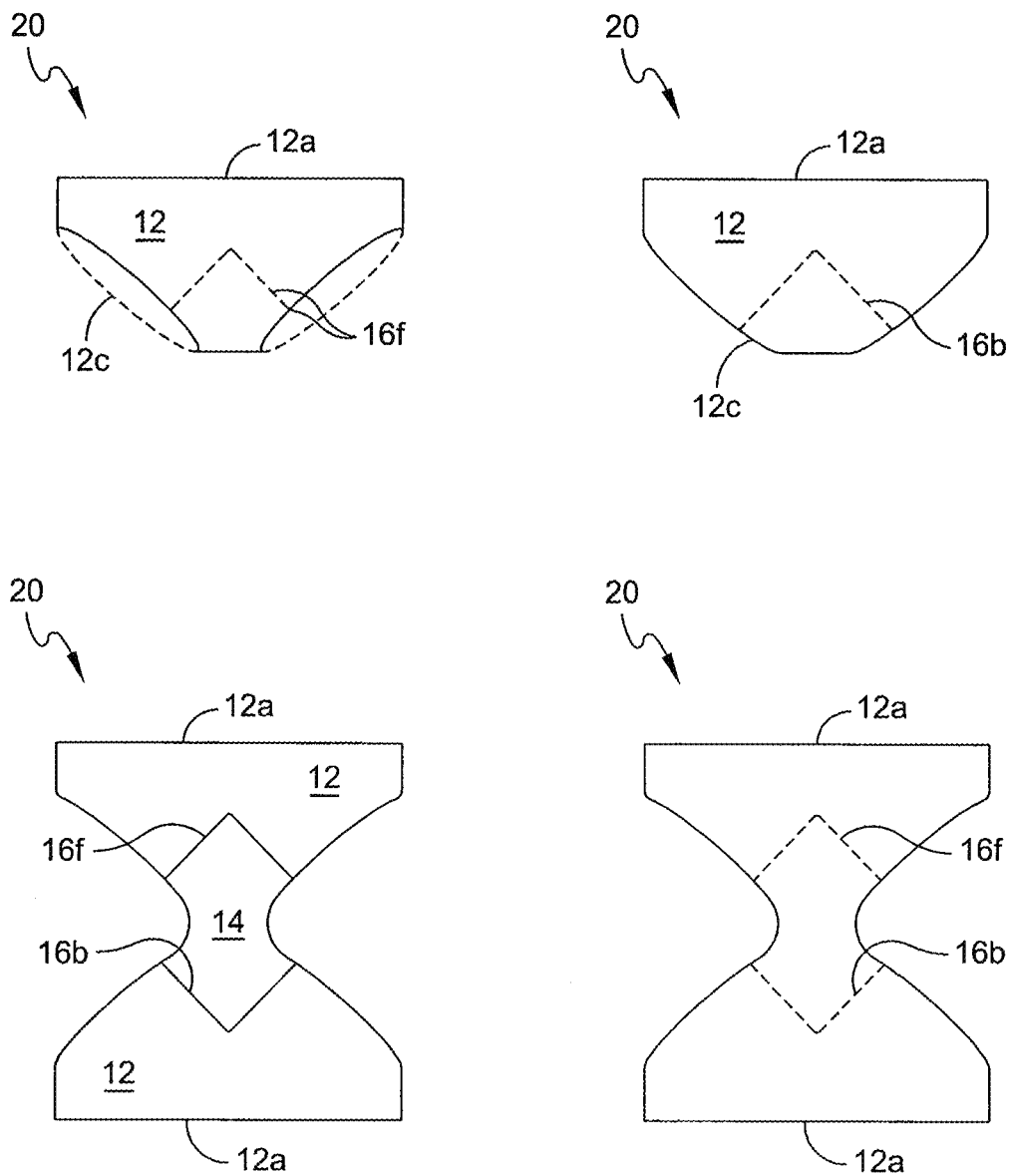
FIG. 2 shows front, back, interior and exterior views of another exemplary garment according to the present disclosure.

Optionally, the shape and position of the front and back seams 16f,b may be varied relative to the upper edge 12a, to accommodate stains are sometimes found in the front and/or back areas of the underwear, especially at the edge of the front and back of sanitary napkins For example, FIG. 2 shows another exemplary embodiment of an undergarment 20 in which the front and back seams 16f,b comprise the shape of an inverted triangular, which assists in preventing leaks, spotting, and stains on the front and back of the underwear.

Figure 3:
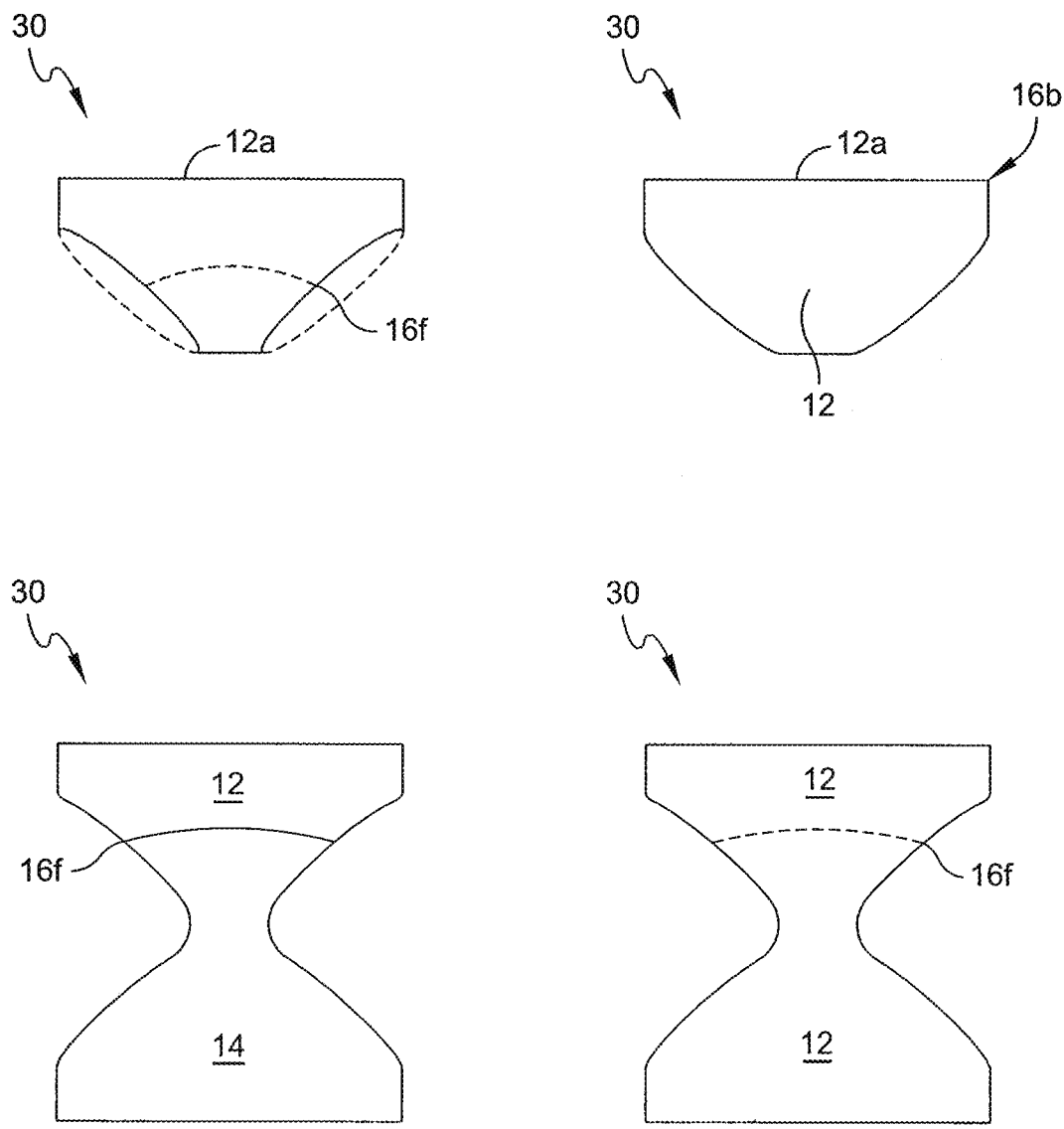
FIG. 3 shows front, back, interior and exterior views of another exemplary garment according to the present disclosure.

Also optionally, gusset 12 can extend to the upper edge 12a of the panty, as shown in FIG. 3. in which the gusset 14 extends up to and is co-terminus with the upper edge 12a of the panty. Alternatively or in addition to, the panty can comprise one piece of fabric continuing to the aforementioned front seam, as shown in FIG. 4.

Figure 4:
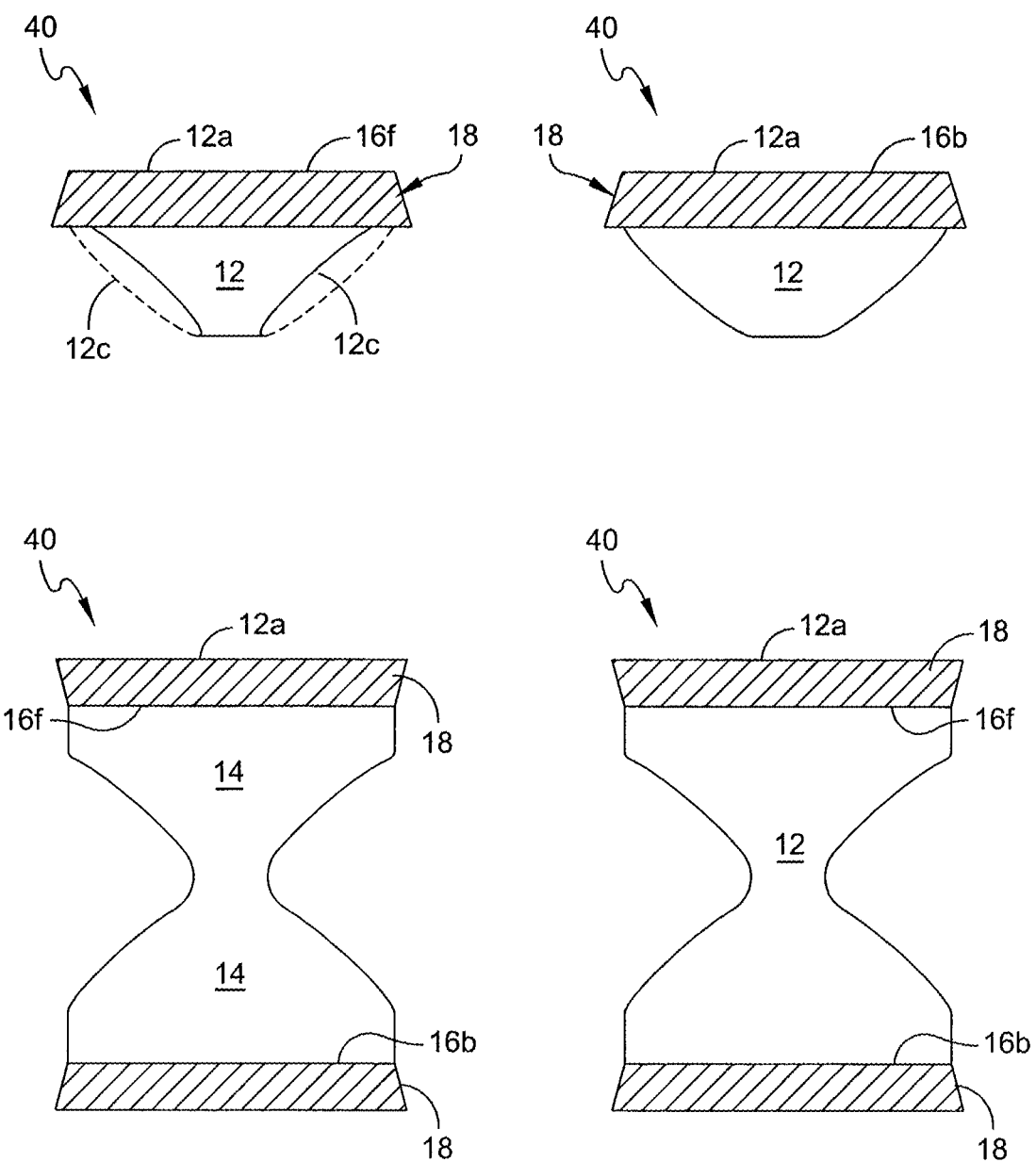
FIG. 4 shows front, back, interior and exterior views of another exemplary garment according to the present disclosure.

FIG. 4 shows another exemplary embodiment of an undergarment 40 according to the present disclosure. To maximize the underwear's function and aesthetics, seams, like those that would be created by underwear designs shown above, may be avoided by constructing the panty so that the entire front to back may be made of the aforementioned functional fabrics. Such a construction involves attaching the gusset 14 at the front and back edges 14a,b to a band 18 of fabric that has a different composition than the main body 12 of the panty. As shown, such fabrics may include lace, silk, chiffon, cotton, or any fabric that may or may not be treated to have functional properties, but more importantly prevents visible panty lines around the waist area. In the present embodiment, the underwear may or may not include a gusset.

In any and all of the foregoing embodiments, the gusset 14 of the undergarment may be composed of one or more separate pieces of fabric that are not bound together. This design allows for the wings of a sanitary pad to be inserted between the separate layers of fabric in a discreet and comfortable way.

One iteration is designed similar to regular non-functional underwear, however, the entire garment may be made of functional fabric (excluding decorative embellishments), with iterations described above, or with no seams such that the entire underwear, excluding the band, is made of one single piece of fabric. By constructing the entire lower side of the underwear with special fabrics, the underwear can protect the wearer of this garment from unwanted stains and leaks without compromising style. However, the upper area of the garment does not need to have such special functionalities, thus it may be made out of any fabric to lower the cost of the garment. This is true unless the fabric on the lower part of the garment has immense wicking capabilities that result in the transfer of fluids to the top band of the garment. Then, the band may be treated with a hydrophobic finish. Even so, this may decrease the overall cost of the garment as compared to the entire underwear constructed with the invented combination of fabrics, and this may increase the aesthetics and functionalities of the underwear.

Any and all of the materials, fabrics, layers and techniques described above may be combined, or may be used individually.

The present disclosure provides fabrics that may be used in the foregoing and other garments. "Fabric," as used herein, refers to a single or multiple layers of fabrics. The present fabric and garment constructions provide unique advantages of stain resistance, fluid retention, fluid absorbency, and garment aesthetics (look, feel, softness and stretch) that are comparable to those of standard (non-protective) undergarments. The garments are not intended to replace feminine hygiene products such as sanitary napkins and tampons, but to complement such products during a woman's menstruation.

The fabric may have a total weight range of less than 7 oz/sq yard up to about 14.6 oz/sq$^2$. The fabric may comprise a top fabric layer or layers with a total absorbent capacity of at least about 300 g/m$^2$ as determined using the Eulie Dip Test, more particularly at least about 800 g/m$^2$, more particularly at least about 1300 g/m$^2$.

It is desirable for the inner layer to absorb fairly rapidly to avoid spills, and thus the inner layer should have an absorbency percentage of at least 10% as determined in ASTM D4772. It is important that the fabric actually absorb into the fibers rather than simply hold liquid like a sponge.

Figure 5:
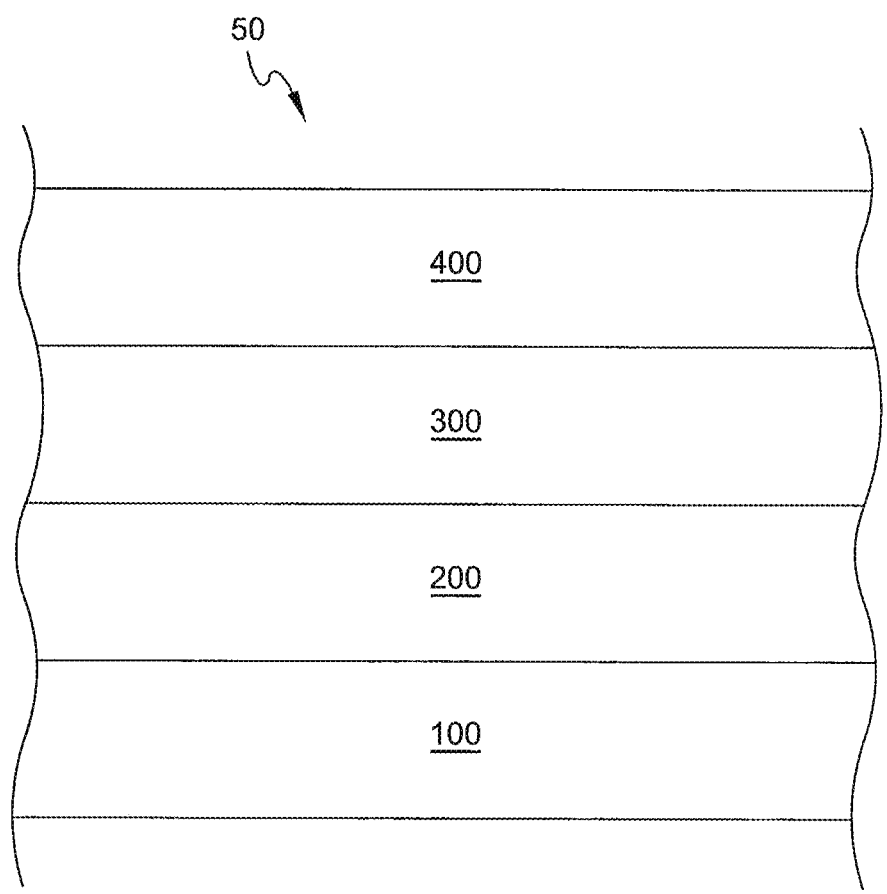
FIG. 5 shows a cross-sectional view of one exemplary multi-layer fabric according to the present disclosure.

FIG. 5 shows one exemplary multi-layer fabric section 50 that can be used in any garment, including any of the foregoing embodiments. Fabric section 50 comprises four layers: a first, body contacting, layer 100; a second, absorbent layer 200 disposed adjacent to the body-contacting layer 100; a third, fluid-resistant or fluid-proof barrier layer 300 disposed adjacent to the absorbent layer 200, opposite layer 100; and, an optional fabric layer 400 that may be included for, among other things, aesthetic reasons.

Layer 100 may be any material that is capable of allowing the transmission of fluid to the absorbing layer 200, and that remains relatively dry even when fluids penetrate its surface. The dryness of layer 100 may be achieved through several methods. For example, when fluid is released on a point source of the inner surface (body-contacting surface) of layer 100, the fabric can distribute the fluid by wicking it across a greater surface area. Alternatively, layer 100 may be non-absorbent, such that fluid is transferred to layer 200, allowing layer 100 to remain free of fluid and, consequently, stains. The stains in layer 200 then become opaque from the perspective of the wearer.

Suitable materials for the layer 100 include, but are not limited to, fabrics made from the following naturally stain-resisting fibers: polyolefin, polyamide, polyester, and combinations thereof. For ease of discussion, the term "stain-releasing," will be used herein to mean both stain-resistant materials and stain-releasing materials, including those that have been treated to be stain-resistant or stain-releasing. Alternatively, the layer 100 can comprise any suitable fabric that has been treated with a stain releasing or resisting finish (such as the Darlington finishes shown in Table A). Layer 100 also can comprise an inherently stain-releasing material such as microfiber or a microfiber blend comprising different materials that can be treated to have even greater stain-releasing capabilities.

Alternatively, or in addition to the foregoing, layer 100 may have a relatively dark color that can assist in masking stains.

The absorbent layer 200 can comprise any material capable of absorbing fluid, and of releasing the absorbed fluid under certain conditions (for example, during a laundry cycle). The absorbent layer can comprise an absorbency of greater than about 300 grams/per square meter ("gm/m$^2$"); more particularly greater than about 800 gm/m$^2$, and more particularly still greater than about 1300 gm/m$^2$.

Suitable materials for the absorbent layer 200 include, but are not limited to, woven or nonwoven microfiber or plastic knits; fabrics formed using hydrophilic fibers, absorbent or superabsorbent foams, fibers or powders.

Alternatively, any knit, absorbent knit, woven, nonwoven or polymeric material that has reservoir properties due to air gaps or voids can be used as the absorbent layer 200. Examples of such materials include, but are not limited to, double needlebar knit fabrics, foams, nonwovens, and the like.

In some embodiments, the absorbent layer 200 can comprise a knitted fabric that has been treated to have hydrophilic properties. Additionally, the yarn from with the knitted fabric is made can be treated to be hydrophilic, prior to knitting. In some embodiments, the yarn and the knitted fabric can both be treated to be hydrophilic.

Alternatively, it is possible that the absorbent layer could be removable and possibly disposable, eliminating the requirement for stain resistance. Such as disposable layer may comprise, for example, a thin absorbent or superabsorbent foam, fabric, nonwoven or composite.

Alternatively, the absorbent layer 200 can be covered with an aesthetic non-staining inner layer 100 that can mask some level of staining, which would then remain invisible to the consumer.

The barrier layer 300 can comprise any material or combinations of materials that prevent or minimize the transmission of fluid through the barrier layer, and that do not adversely affect the feel and/or hand of the garment.

While many materials may be used in combination for the barrier layer, we devised a unique test for measuring elongation and have found that the use of fabrics or nonwovens elongations comparable to the Darlington fabrics listed in Table A to be effective.

By having an inner layer capable of absorbing the specified quantity of fluids, the hydrostatic pressure resistance of the barrier layer can be limited, which allows more latitude with creating desirable aesthetics.

Some suitable materials for the barrier layer 300 include, but are not limited to, a fabric laminated to a polymer film. The polymer film can comprise a thickness of less than or equal to about 15 microns, more particularly less than or equal to about 10 microns, and more particularly still less than or equal to about 5 microns. Suitable materials for the polymer film include, but are not limited to, copolyetheresters, hytrels, nylons, polyolefins, and other soft elastic TPE could be used if they have sufficient softness and pliability to be used in an undergarment. The polymer film may be laminated in a 2-ply or 3-ply configuration, or may be free-hanging and sewn between other layers (such as an absorbant layer and an aesthetic layer). One suitable polymer material is a highly moisture transmittable monolithic polyurethane film sold by Omniflex Inc. of Greenfield, Mass. under the name TX1540.

Other suitable materials for the barrier layer 300 include, but are not limited to, a 2-ply laminate polymer film protected by another layer, which is not bonded to the film, as this allows for a softer feel in the finished garment. The film/composite may also be treated with a hydrophobic (water-repellent) treatment to enhance the barrier properties without negatively impacting the hand. Also, in still another embodiment, the barrier film or composite can be pressed with heat and/or pressure into the surrounding layers to enhance feel, or is stretched. This heat/pressure or stretching treatment also has the advantage of creating small fissures to enhance breathability.

Other suitable materials for barrier layer 300 can comprise a hydrophobic fabric, which may be inherently hydrophobic, or it may be treated to make it hydrophobic. Suitable fabrics for treating with such hydrophobic coatings include, but are not limited to, relatively tightly knitted, nonwoven or woven fabrics. Suitable hydrophobic materials for treating the fabric include, but are not limited to, polymers such as silicone, polyurethane and combinations thereof. In many cases it is desirable to use elastic polymers for this purpose, such as Lycra and blends thereof. It may be desirable for the hydrophobic treated knitted, nonwoven or woven material to contain microfibers, as this creates a more tortuous path for any fluid to penetrate.

If the material used to form the barrier layer is nonwoven, the use of a meltblown nonwoven may be desirable since it also creates a tortuous path for fluids. Multiple nonwoven, knits or wovens may also be combined in any number of layers, and various or all layers may be treated with hydrophobic treatment or made of naturally hydrophobic material(s). In cases where these treated (non-film) materials are used in the concept there may be the advantage of greater breathability than may be achieved with a film barrier. One exemplary barrier layer is an elastic meltblown nonwoven material made from a co polyether-ester polymer similar to the product that was once sold by Kimberly Clarke under the brand name Demique.

Other suitable barrier layers 300 can comprise a microporous polymer film. Suitable microporous polymer films include, but are not limited to, urethane films, PTFE films, polyolefin films, and combinations thereof. One microporous urethane film is sold by Porvair of England. Suitable microporous PTFE films are available under the product name Goretex. The foregoing microporous films can be used in any combination of layers, either laminated or unlaminated, and can be treated with a hydrophobic water repellent treatment, or filled with a substance such as oil, to keep the pores from becoming contaminated.

Any type of material can be used as the optional aesthetic layer 400. Examples of suitable materials for layer 400 include, but are not limited to, lace, silk, chiffon, cotton, polyester, nylon, LYCRA®, and the like, and blends and combinations thereof. If desired, the fabric can be colored, printed, etc., and may be treated to have any of the functional properties described herein.

Figure 6:
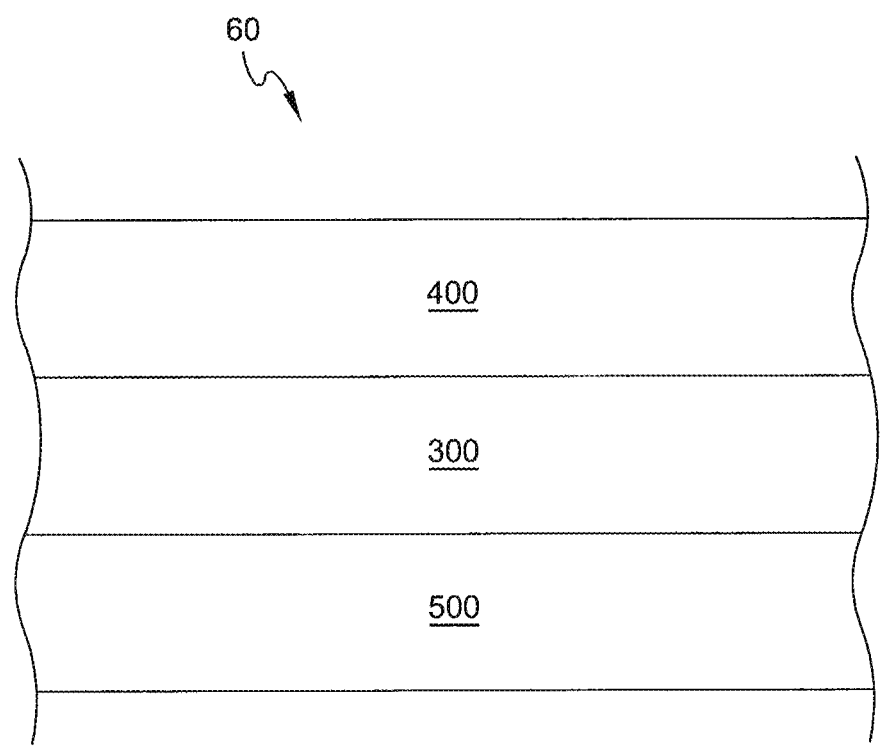
FIG. 6 shows a cross-sectional view of an other exemplary multi-layer fabric according to the present disclosure.

FIG. 6 shows another exemplary multi-layer fabric section 60 that can be used in the present garments, comprising three layers: a first, body contacting and absorbent layer 500; a second, fluid-resistant or fluid-proof barrier layer disposed adjacent to the absorbent layer, opposite layer 300; and, optional fabric layer 400. Suitable materials for layers 300 and 400 are the same as those described above.

Suitable materials for layer 500 include any material that is both stain-resistant and that is capable of absorbing fluid and, under certain conditions, releasing the fluid. Examples of suitable materials for layer 500 include materials discussed above with respect to layer 200, one surface (the body-contacting surface) of which has been treated with a material that imparts stain resistance. An example of such a treatment would be the Darlington treatments listed in Table A, but could also be any similar treatment.

Figure 7:
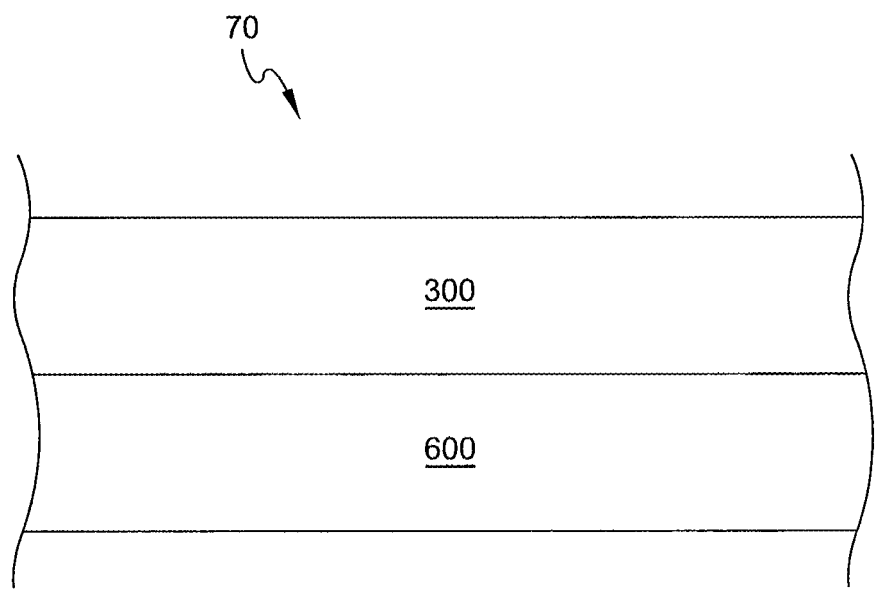
FIG. 7 shows a cross-sectional view of another exemplary dual-layer fabric according to the present disclosure.

FIG. 7 shows another exemplary dual-layer fabric section 70 that can be used in the present garments, comprising a first, body contacting layer 600 and an optional fabric layer 400. The functional features of the present concept may all be combined in a single layer of fabric 600 that combines fluid absorption and barrier characteristics and, in some instances, stain-releasing characteristics. Such a fabric may be constructed of one or more fibers with one or more of the foregoing characteristics, to combine the characteristics of the different fibers to achieve the desired undergarment properties. In some cases, it may be desirable for a single fabric layer to have the opposing surfaces of the fabric faced with different types of fibers, each having different characteristics (e.g., one fiber that is hydrophobic and absorbent, one fiber that is hydrophilic).

For example, layer 600 can comprise a single layer of fabric comprising a first surface that is stain resistant (naturally, or as a result of being treated with a stain resistant treatment, as described above) and absorbent, and a second surface that is hydrophobic. The first surface can be capable of absorbing an amount of fluid between about 0.1 milliliters ("ml") and about 50 ml of fluid within as little as 95 cm$^2$ up to the entire surface area of the undergarment, and more particularly between about 3 ml and about 15 ml of fluid. The second, opposite surface of the layer can be treated to be hydrophobic (as described above) and to prevent or minimize the transmission of the absorbed fluids. The second surface may be treated with traditional DWR treatments (such as Zepel or other treatments) and/or it may be saturated or impregnated with a hydrophobic polymer (such as silicone or urethane). The hydrophobic polymer fills the gaps in the fabric, and may be applied by dip and squeeze, knife over roll, spray, gravure, or other methods. The fabric used may be, for example, a knit and with the stretch characteristics described above. The fabric may also include the use of microfiber.

Improved performance may be obtained by bonding the seams together without stitching using tape or adhesive seams, or using sealants over the stitched seams. Suitable materials include elastic polymer sealants and adhesives. Seams can be sealed with seam tape such as Worthen Industries Tape 375-4, using a Pfaff seam sealing machine to eliminate sewing the edges of the gusset together or to the body of the garment. Non-wicking thread may also be used to minimize or eliminate blood from wicking along the thread in stitched seams.

In any and all of the embodiments disclosed herein, two or more of layers 100 through and including 600 may be attached at least partially to each other using a variety of techniques, in order to reduce the number of layers in the garments. For example, the layers may be laminated to form a single, composite layer, or they may be attached by sewing at various attachment points, so that the separate layers remain detached in between the seams.

Also, any or all of the materials and/or material surfaces in the undergarments can comprise an active agent, such as an antimicrobial or antifungal material. Example of suitable active agents include, but are not limited to, ionic silver, copper, zinc, nanoparticles thereof, and combinations thereof (which act as a natural antimicrobials). The use of nanoparticles does not compromise the aesthetics of the garments, which is important for undergarments. The active agents can be added to any layer of fabric or film or in fact into the adhesive if one is used for bonding. The addition of phase-change microspheres may also be used to add a temperature-regulating feature.

The foregoing fabrics and composites facilitate the construction of many garments, particularly aesthetically pleasing and protective women's undergarments. The undergarment designs may be slightly different from non-protective undergarments to aid in leak and stain prevention, while simultaneously being aesthetically pleasing. Accordingly, the foregoing materials and methods of construction may be applied to styles that characterize regular non-protective undergarments, such as briefs, thongs, boy shorts, and the like. Existing "period" underwear is either designed such that the protective gusset is of regular size or the protective gusset extends to the back waistband in a fashion that is unappealing. The present concept provides designs are functional in preventing leaks and stains but are also aesthetically pleasing.

The functional fabrics discussed above have many other uses including but not limited to regular women's and men's apparel, men's functional apparel, industrial fabrics, sporting apparel, and protective apparel. The garment and fabric constructions described herein are designed for use in protective intimate apparel to absorb and/or contain bodily discharges and to resist staining and/or release staining when laundered, while not negatively impacting the look, feel and breathability for use in intimate apparel and other clothing. The garments and construction methods described herein may be used for a variety of garments including but not limited to underwear, bras, bathing suits, and outerwear.

While one use for this unique combination of materials is for protective panties during menstruation, the present concept may also be used for underwear and outerwear preventing leaks and stains during pregnancy, post-partum, menopause, and post-menopause. The capabilities may be used separately or combined in panties, bras, outer clothing, bathing suits, and the like. The potential wicking capabilities may be used specifically in, but not limited to, outerwear and sleepwear for menopausal women. In addition, pregnant and post-partum women often experience unexpected lactation, causing uncomfortable and embarrassing stains and/or leaks on bras and/or outer garments. The use of this concept for construction of nursing bras can alleviate this inconvenience. Pregnant and post-partum women also experience heavy vaginal bleeding during pregnancy and after giving birth, creating a strong need for stain releasing and leak proof products. In addition, pre-teen girls often experience anxiety about menstruating for the first time. The present materials and construction techniques provide garments that would allow them to feel at ease knowing they are protected from potential leaks or stains.

WORKING EXAMPLES

Fabric Testing

Two categories of fabrics were tested for use in the present garments: absorbent (hydrophilic) fabrics and repellent (hydrophobic) fabrics. Table A summarizes the fabric and yarn type and treatment, if any, as well as the manufacturer's reported fabric weight, the total water absorbency (as determined by the "Eulie Dip Test," discussed below), and the measured Absorbent capacity (as determined by the "Eulie Capacity Test, discussed below). Throughout the Tables, the absorbent layer fabrics are referred to by a letter designation A, B or C, and the repellent layer fabrics are referred to by a numeric designation 3, 4 or 5.

Eulie Dip Test

As noted above, the total water absorbency of each fabric was tested using the Eulie Dip Test, which involves measuring, cutting and weighing a five inch by five inch (5"×5") dry piece of fabric. The fabric piece was then fully submerged in water for 15 seconds, after which it was removed from the water while holding only the upper corners. The excess water was allowed to drain from the fabric piece for twenty-five (25) seconds, after which the fabric piece was weighed a second time. The total water absorbency was calculated by subtracting the dry fabric weight from the wet fabric weight, as shown in Table A.

Eulie Capacity Test

Also as noted above, the absorbent capacity of each fabric was tested using the Eulie Capacity Test, which involves which involves measuring, cutting and weighing a five inch by five inch (5"×5") dry piece of fabric. The fabric section was disposed on an angled surface of five (5) degrees, and the tip of a titration tube was disposed one (1) centimeter (cm) above the fabric surface, four (4) cm from the upper edge of the fabric section, centered on both sides of the fabric section. Fluid (water containing green food coloring) was dispensed from the titration tube at a flow rate of approximately 20 milliliters/minute. Fluid flow was discontinued when water ran off the edge of the fabric section, or when water reached all four corners of the fabric section. The absorbent capacity listed in Table A represents the total volume of water dispensed from the titration tube.

Functional Trials

The fabrics listed in Table A were used to construct panties for Functional Trials by women during their menstrual cycle. The panties were constructed by forming gussets with various combinations of the fabrics listed in Table A, which then were stitched over the gusset region of various branded panties (e.g., Hanes®, etc.).

The panties were forwarded to volunteer testers. The testers wore the panties while menstruating, and recorded the amount of time that the panties were worn and the amount of time between wearing and washing the panties. After washing, a record of any remaining stains was recorded by the testers, along with qualitative remarks about the comfort and effectiveness of the panties.

There was an aesthetic trade off when the gusset became too bulky or thick due to multiple layers. Therefore, it is desirable to provide the maximum amount of absorbent capacity per thickness or weight of the absorbent layers. Some of the best performing composites from the functional trial included 3 layers of thin absorbent layer "A" (Example 1), but a single absorbent layer C (Example 6) also appears to perform well.

Fabric A appeared to absorb liquids initially faster than Fabric B, resulting in fewer instances of "puddling" or "pooling" directly above the repellent fabric.

Fabric 3 appears to have provided better leakage protection than Fabric 4, likely due to the slightly higher weight of Fabric 3.

The results of the panty tests showed that the performance was dependent upon a variety of factors including the hand, weight, absorbency and perceived thickness of the gusset.

Throughout the application, it should be noted that the terms "first," "second," and the like herein do not denote any order or importance, but rather are used to distinguish one element from another, and the terms "a" and "an" herein do not denote a limitation of quantity, but rather denote the presence of at least one of the referenced items. Similarly, it is noted that the terms "bottom" and "top" are used herein, unless otherwise noted, merely for convenience of description, and are not limited to any one position or spatial orientation. In addition, the modifier "about" used in connection with a quantity is inclusive of the stated value and has the meaning dictated by the context (e.g., includes the degree of error associated with measurement of the particular quantity).

Compounds are described using standard nomenclature. For example, any position not substituted by an indicated group is understood to have its valency filled by a bond as indicated, or a hydrogen atom A dash ("—") that is not between two letters or symbols is used to indicate a point of attachment for a substituent. For example, —CHO is attached through carbon of the carbonyl group. Unless defined otherwise herein, all percentages herein mean weight percent ("wt. %"). Furthermore, all ranges disclosed herein are inclusive and combinable (e.g., ranges of "up to about 25 weight percent (wt. %), with about 5 wt. % to about 20 wt. % desired, and about 10 wt. % to about 15 wt. % more desired," are inclusive of the endpoints and all intermediate values of the ranges, e.g., "about 5 wt. % to about 25 wt. %, about 5 wt. % to about 15 wt. %", etc.). The notation "+/−10%" means that the indicated measurement may be from an amount that is minus 10% to an amount that is plus 10% of the stated value. Finally, unless defined otherwise, technical and scientific terms used herein have the same meaning as is commonly understood by one of skill in the art to which this disclosure belongs.

While the disclosure has been described with reference to an exemplary embodiment, it should be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure not be limited to the particular embodiment disclosed as the best mode contemplated for carrying out this disclosure, but that the disclosure will include all embodiments falling within the scope of the appended Claims.

What is claimed is:

1. An undergarment portion, comprising:
    an absorbent layer comprising a body-contacting surface, the absorbent layer having an absorbent capacity of at least about 300 g/m$^2$, the absorbent layer configured to absorb between about 0.1 ml and about 50 ml of liquid, wherein the liquid is absorbed into fibers of the absorbent layer, the liquid being distributed across the absorbent layer via wicking; and
    a hydrophobic layer disposed adjacent to the absorbent layer, the hydrophobic layer comprising an outer surface disposed on an opposite side of the absorbent layer from the body-contacting surface, the hydrophobic layer formed of a tightly knitted woven or nonwoven fabric having a weight of between about 5.2 oz/yd$^2$ and about 7.2 oz/yd$^2$, the fabric having fibers that have been coated or saturated with an elastic water repellent polymer, wherein the hydrophobic layer has a limited hydrostatic pressure resistance and is configured to limit transmission of liquid through the hydrophobic layer when a volume of liquid is between about 0.1 ml and about 50 ml, but allow liquid to pass through the hydrophobic layer when the volume of liquid is greater than 50 ml.

2. The undergarment portion of claim 1, wherein the absorbent layer is formed of a knit fabric.

3. The undergarment portion of claim 1, wherein one or both surfaces of the absorbent layer comprises a napped, sueded or texturized surface.

4. The undergarment portion of claim 1, wherein one or both surfaces of the hydrophobic layer comprises a napped, sueded or texturized surface.

5. The undergarment portion of claim 1, wherein the absorbent layer comprises first and second layers, wherein the second layer is positioned adjacent to the first, body-contacting layer, wherein the body-contacting layer is adapted to absorb fluid and to wick the absorbed fluid through to the adjacent layer.

6. The undergarment portion of claim 1, wherein the hydrophobic layer comprises a water repellant finish.

7. The undergarment portion of claim 1, wherein the absorbent layer and the hydrophobic layer are bonded together.

8. The undergarment portion of claim 7, wherein the absorbent layer and the hydrophobic layer are bonded together at an edge of each layer.

9. The undergarment portion of claim 1, wherein the undergarment portion has a weight of less than about 20 oz/yd$^2$.

10. The undergarment portion of claim 1, wherein the undergarment portion is a gusset portion of the undergarment.

11. The undergarment of claim 10, wherein the gusset comprise a front edge, a side, a back edge and opposing side edges, and the front and back edges are attached to a front and a back of the undergarment at a front seam and a back seam.

12. The undergarment of claim 10, wherein one or more of the front and back seams comprise an inverted triangular shape.

13. The undergarment of claim 10, wherein one or more of the front and back seams extend to an upper edge of the undergarment.

14. The undergarment of claim 13, wherein one or more of the front and back seams and one or more of the opposing edges comprises a hydrophobic coating.

15. The undergarment portion of claim 1, wherein the hydrophobic layer is an outermost layer of the undergarment.

16. The undergarment portion of claim 1, wherein the hydrophobic layer includes spandex and at least one of cotton and nylon.

17. The undergarment of claim 1, wherein the hydrophobic layer includes first and second hydrophobic layers, wherein each layer is formed of a tightly knitted woven or nonwoven fabric having a weight of between about 5.2 oz/yd2 and about 7.2 oz/yd.

18. An undergarment portion, comprising:
    an absorbent layer comprising a body-contacting surface, the absorbent layer configured to absorb between about 0.1 ml and about 50 ml of liquid, wherein the liquid is absorbed into fibers of the absorbent layer, the liquid being distributed across the absorbent layer via wicking; and
    a hydrophobic layer disposed adjacent to the absorbent layer, the hydrophobic layer comprising an outer surface disposed on an opposite side of the absorbent layer from the body-contacting surface, the hydrophobic layer formed of a tightly knitted woven or nonwoven fabric having a weight of between about 5.2 oz/yd$^2$ and about 7.2 oz/yd$^2$, the fabric having fibers that have been coated or saturated with an elastic water repellent polymer, wherein the hydrophobic layer has a limited hydrostatic pressure resistance and is configured to limit transmission of liquid through the hydrophobic layer when a volume of liquid is between about 0.1 ml and about 50 ml, but allow liquid to pass through the hydrophobic layer when the volume of liquid is greater than 50 ml;
    wherein the undergarment portion has a weight of less than about 20 oz/yd$^2$.

19. The undergarment portion of claim 18, wherein the hydrophobic layer is an outermost layer of the undergarment.

20. The undergarment portion of claim 18, wherein the hydrophobic layer includes spandex and at least one of cotton and nylon.

21. The undergarment of claim 18, wherein the hydrophobic layer includes first and second hydrophobic layers, wherein each layer is formed of a tightly knitted woven or nonwoven fabric having a weight of between about 5.2 oz/yd2 and about 7.2 oz/yd.

22. An undergarment portion, comprising:
- an absorbent layer comprising a body-contacting surface, the absorbent layer configured to absorb between about 0.1 ml and about 50 ml of liquid, wherein the liquid is absorbed into fibers of the absorbent layer, the liquid being distributed across the absorbent layer via wicking; and
- a hydrophobic layer disposed adjacent to the absorbent layer, the hydrophobic layer comprising an outer surface disposed on an opposite side of the absorbent layer from the body-contacting surface, the hydrophobic layer formed of a tightly knitted woven or nonwoven fabric having a weight of between about 5.2 oz/yd$^2$ and about 7.2 oz/yd$^2$, the fabric having fibers that have been coated or saturated with an elastic water repellent polymer, wherein the hydrophobic layer has a limited hydrostatic pressure resistance and is configured to limit transmission of liquid through the hydrophobic layer when a volume of liquid is between about 0.1 ml and about 50 ml, but allow liquid to pass through the hydrophobic layer when the volume of liquid is greater than 50 ml.

23. The undergarment portion of claim 22, wherein the hydrophobic layer is an outermost layer of the undergarment.

24. The undergarment portion of claim 22, wherein the hydrophobic layer includes spandex and at least one of cotton and nylon.

25. The undergarment of claim 22, wherein the hydrophobic layer includes first and second hydrophobic layers, wherein each layer is formed of a tightly knitted woven or nonwoven fabric having a weight of between about 5.2 oz/yd2 and about 7.2 oz/yd.

* * * * *